United States Patent
Peralta et al.

(10) Patent No.: US 10,639,456 B2
(45) Date of Patent: May 5, 2020

(54) GUIDEWIRE WITH TORQUE TRANSMISSION ELEMENT

(71) Applicant: MicroVention, Inc., Tustin, CA (US)

(72) Inventors: Nelson Peralta, Tustin, CA (US); Ngoclan H. Nguyen, Stanton, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 254 days.

(21) Appl. No.: 15/278,795

(22) Filed: Sep. 28, 2016

(65) Prior Publication Data

US 2017/0087340 A1 Mar. 30, 2017

Related U.S. Application Data

(60) Provisional application No. 62/233,951, filed on Sep. 28, 2015.

(51) Int. Cl.
*A61M 25/09* (2006.01)

(52) U.S. Cl.
CPC ........ *A61M 25/09041* (2013.01); *A61M 2025/09083* (2013.01)

(58) Field of Classification Search
CPC ........ A61M 2025/09058–09091; A61M 25/09
See application file for complete search history.

(56) References Cited

U.S. PATENT DOCUMENTS

| | | | |
|---|---|---|---|
| 5,601,600 A | 2/1997 | Ton | |
| 6,454,780 B1 | 9/2002 | Wallace | |
| 6,478,773 B1 | 11/2002 | Gandhi et al. | |
| 6,500,149 B2 | 12/2002 | Gandhi et al. | |
| 6,807,446 B2 | 10/2004 | Fenn et al. | |
| 6,849,081 B2 | 2/2005 | Sepetka et al. | |
| 6,855,125 B2 | 2/2005 | Shanley | |
| 6,966,892 B2 | 11/2005 | Gandhi et al. | |
| 7,001,422 B2 | 2/2006 | Escamilla et al. | |
| 7,048,719 B1 | 5/2006 | Monetti | |
| 7,166,122 B2 | 1/2007 | Aganon et al. | |
| 7,344,558 B2 | 3/2008 | Lorenzo et al. | |
| 7,651,513 B2 | 1/2010 | Teoh et al. | |
| 7,691,121 B2 | 4/2010 | Rosenbluth et al. | |
| 7,722,552 B2 * | 5/2010 | Aimi | A61M 25/09 600/585 |
| 8,157,751 B2 * | 4/2012 | Adams | A61M 25/005 600/585 |
| 8,182,506 B2 | 5/2012 | Fitz et al. | |
| 8,192,480 B2 | 6/2012 | Tieu et al. | |
| 8,348,860 B2 * | 1/2013 | Murayama | A61M 25/09 600/585 |
| 8,460,332 B2 | 6/2013 | Tieu et al. | |
| 9,242,070 B2 | 1/2016 | Tieu | |
| 2002/0188341 A1 | 12/2002 | Elliott | |
| 2003/0045901 A1 | 3/2003 | Opolski | |

(Continued)

FOREIGN PATENT DOCUMENTS

WO  WO 2002/055146 A1  7/2002

*Primary Examiner* — Devin B Henson
*Assistant Examiner* — Huong Q Nguyen
(74) *Attorney, Agent, or Firm* — Inskeep IP Group, Inc.

(57) ABSTRACT

A guidewire includes a shaft element and a flexible distal torque transmission element. The torque transmission element can be formed of a coiled wire having one or more of the loops that are welded or otherwise fixed together to achieve desirable flexibility and torque transmission.

3 Claims, 5 Drawing Sheets

(56) References Cited

U.S. PATENT DOCUMENTS

| | | |
|---|---|---|
| 2004/0034363 A1 | 2/2004 | Wilson et al. |
| 2005/0149108 A1 | 7/2005 | Cox |
| 2006/0025803 A1 | 2/2006 | Mitelberg et al. |
| 2006/0116708 A1 | 6/2006 | Ogawa et al. |
| 2006/0173488 A1 | 8/2006 | Takeuchi et al. |
| 2006/0241682 A1 | 10/2006 | Kurz |
| 2006/0271098 A1 | 11/2006 | Peacock, III |
| 2007/0055302 A1 | 3/2007 | Henry et al. |
| 2009/0054905 A1 | 2/2009 | Levy |
| 2009/0156999 A1* | 6/2009 | Adams ............... A61M 25/005 604/103.09 |
| 2009/0163780 A1 | 6/2009 | Tieu |
| 2010/0094395 A1 | 4/2010 | Kellett |
| 2010/0106162 A1 | 4/2010 | Jaeger et al. |
| 2010/0268204 A1 | 10/2010 | Tieu et al. |
| 2011/0046282 A1 | 2/2011 | Mizuta et al. |
| 2013/0245745 A1 | 9/2013 | Vong et al. |

\* cited by examiner

GUIDEWIRE WITH TORQUE TRANSMISSION ELEMENT

RELATED APPLICATIONS

This application claims priority to U.S. Provisional Application Ser. No. 62/233,951 filed Sep. 28, 2015 entitled Guidewire with Torque Transmission Element, which is hereby incorporated herein by reference in its entirety.

BACKGROUND OF THE INVENTION

Many interventional procedures utilize guidewires in order to locate a target treatment site within the vasculature and to help convey treatment material to the treatment site.

Guidewires are typically used in interventional procedures to guide a catheter to a specific treatment site. A user manipulates the guidewire from a proximal location through the vasculature until the guidewire's distal end reaches a desired target location. The catheter is then tracked over the guidewire until the catheter reaches the target location. The guidewire typically should have good pushability (i.e., the ability to be pushed without bending or kinking) as well as the flexibility to navigate tricky bends without getting caught. Additionally, since the user will frequently torque or rotate the guidewire to navigate the complex network of blood vessels, good torque transmission is also an important element of guidewire performance.

SUMMARY OF THE INVENTION

A guidewire is described, comprising a shaft element and a torque transmission element.

In one embodiment, the guidewire comprises a torque transmission element that has some adjacent loops welded or fixed together and other adjacent loops otherwise unconnected.

In another embodiment, the guidewire comprises a torque transmission element comprising a helical coil forming a plurality of loops that are selectively attached to each other via weld points that are positioned in a longitudinal pattern of circumferential locations along at least a portion of the length of the helical coil to decrease the flexibility of the helical coil.

In one embodiment, the guidewire comprises a torque transmission element that is gapped in one or more locations and contiguous in one or more locations. The one or more contiguous locations are formed by connecting portions of the torque transmission element together. The location of the contiguous segments of the torque transmission element can be customized to vary the flexibility, strength, and/or torquability of the guidewire.

In one embodiment, the guidewire comprises a shaft element and a torque transmission element. The shaft element may contain a reduced-diameter portion to accommodate placement of the torque transmission element over the reduced-diameter portion. In one embodiment, the torque transmission element directly contacts the reduced-diameter portion. In another embodiment, the torque transmission element does not contact the reduced diameter portion—but instead contacts a different portion of the shaft element or one or more connecting structures connected to the shaft element. In one embodiment, the guidewire includes a coating layer.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
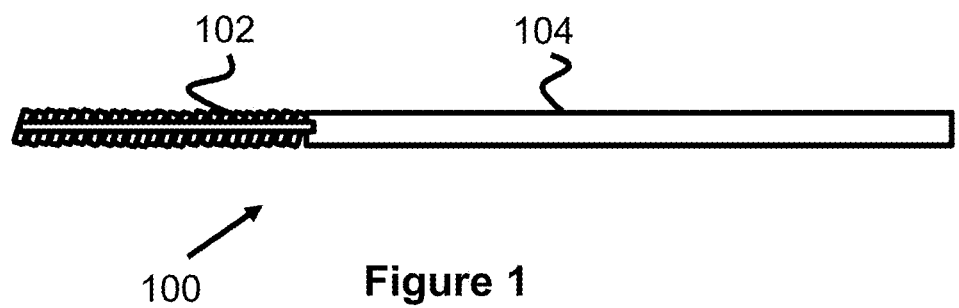
FIG. 1 illustrates an embodiment of a guidewire having a shaft element and a torque transmission element according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIG. 1 illustrates an embodiment of a guidewire 100 according to the present invention, which includes a flexible torque transmission element 102 element that is on a distal portion of an elongate shaft element 104 or fixed to the distal end of the elongated shaft element 104 (note: the left direction is distal and the right direction is proximal in the figures). Prior art guidewires typically fall into two categories. The first category of guidewires is formed from a single solid piece. To increase flexibility on the distal end of the guidewire, cuts or fenestrations are made to the distal end of the guidewire to be more flexible. A second category of guidewires attach a softer tip to the end of the guidewire to provide more flexibility at the tip for navigation purposes. However, both categories of guidewires still suffer from being not flexible enough to navigate around complex turns in the vasculature and/or provide sufficient torquability to transmit torque from the proximal end of the guidewire to the distal end of the guidewire. The present invention discloses an improved guidewire and a method of manufacturing guidewires to provide a better balance of flexibility and torquability. Moreover, the present invention describes a way to easily customize the guidewire for different locations in the human vasculature.

The torque transmission element 102 is preferably composed of one or more helical coils that are welded or otherwise attached to each other in various patterns to provide varying levels of flexibility and torque transmission from the proximal end of the guidewire 100. The coils are comprised of a plurality of windings or loops 107 which are located adjacent to each other. The shaft element 104 is preferably composed of one or more solid or tubular components that provide relative strength and kink-resistance. Hence, much of the guidewire 100 exhibits desirable pushability characteristics, while the distal end of the guidewire 100 exhibits relative flexibility, softness, and ability to convey torque.

Figure 2:
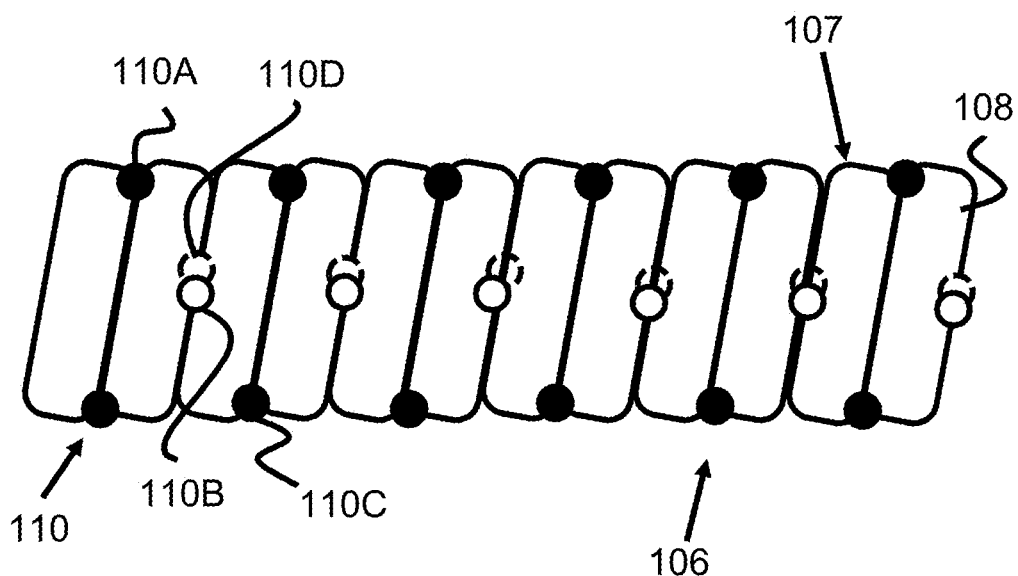
FIGS. 2-3 illustrate an embodiment of a torque transmission element according to the present invention.
Figure 3:
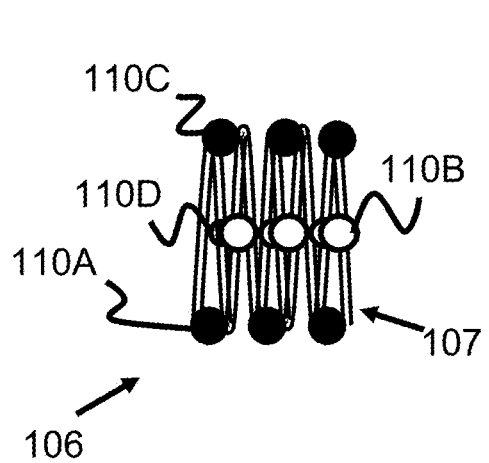
Figure 4:
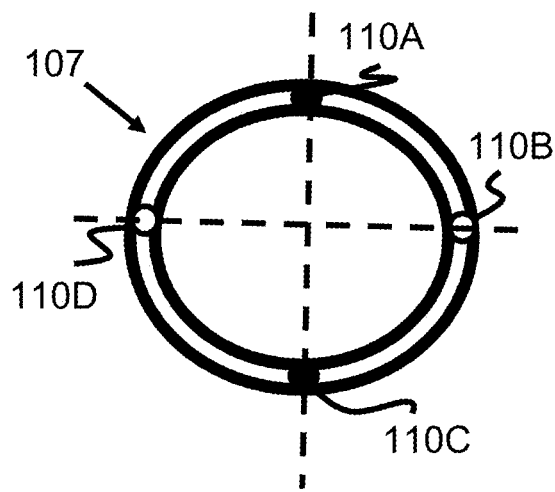
FIG. 4 illustrates an axial end view of a coil and angular weld locations according to the present invention.

FIGS. 2 and 3 illustrate one embodiment of a torque transmission element 106 having a repetitive pattern of weld points 110 that connect adjacent loops 107 of wire 108 together. While the weld points 110 are all generally similar to each other, they are labeled with different reference numerals according to their circumferential location according to FIG. 4, as if axially viewing the torque transmission element (i.e., a top view of a loop of the helically coiled wire 108 of the torque transmission element 106). Specifically, weld point 110A is located at 0 degrees, weld point 110B is located at 90 degrees, weld point 110C is located at 180 degrees, and weld point 110D is located at 270 degrees.

The torque transmission element 106 alternates between first two weld points 110 that are directly, circumferentially opposite of each other, and second two weld points 110 that are directly, circumferentially opposite of each other and perpendicularly oriented to the first two weld points 110. More specifically, referring to the loops 107 of FIG. 2 from left to right, a first and second loop have a 0-degree weld point 110A and a 180-degree weld point 110C. The second and third loops have a 90-degree weld point 110B and a 270-degree weld point 110D. The third and fourth loops have a 0-degree weld point 110A and a 180-degree weld point 110C. In this respect, the pattern of welds at various 90 degree locations proceeds along at least a portion of the torque transmission element 106.

In the present torque transmission element 106 embodiment, the pattern of weld points 110 connects each loop or coil with proximal and distal adjacent loops. In some embodiments, such a pattern may be such that one or more loops are not connected to adjacent loops. In such a pattern, the unconnected loop may not necessarily be in intimate contact with its adjacent, unconnected loops. In other words, such a loop may be spaced apart or gapped relative to its adjacent loops. In this regard, such a pattern may create a torque transmission element with some regions that have gaps between adjacent loops and other regions that have no such gaps.

Figure 5:
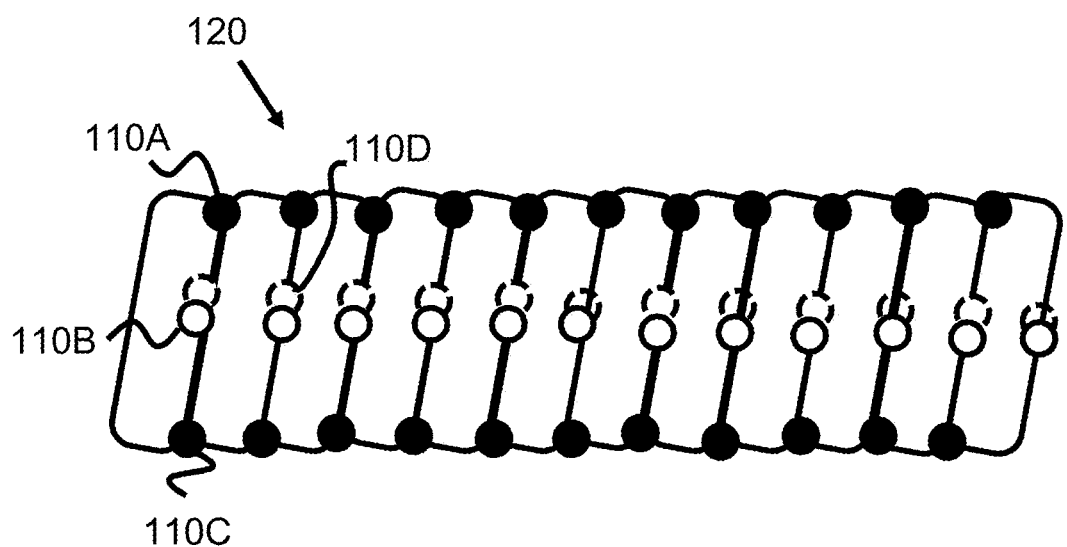
FIGS. 5-7 illustrate side views of different torque transmission elements according to the present invention.

FIG. 5 illustrates another embodiment of a torque transmission element 120 with a different and more frequent weld point 110 pattern than that of element 106. Specifically, the first and second loops have a 0-degree weld point 110A, a 180-degree weld point 110C, a 90-degree weld point 110B, and a 270-degree weld point 110D. The second and third loops have the same weld points 110 as between the first and second loops. Again, this pattern proceeds over at least a portion of the torque transmission element 120. The more frequent weld points 110 relative to previously described element 106 create less flexibility and greater bend strength.

Figure 6:
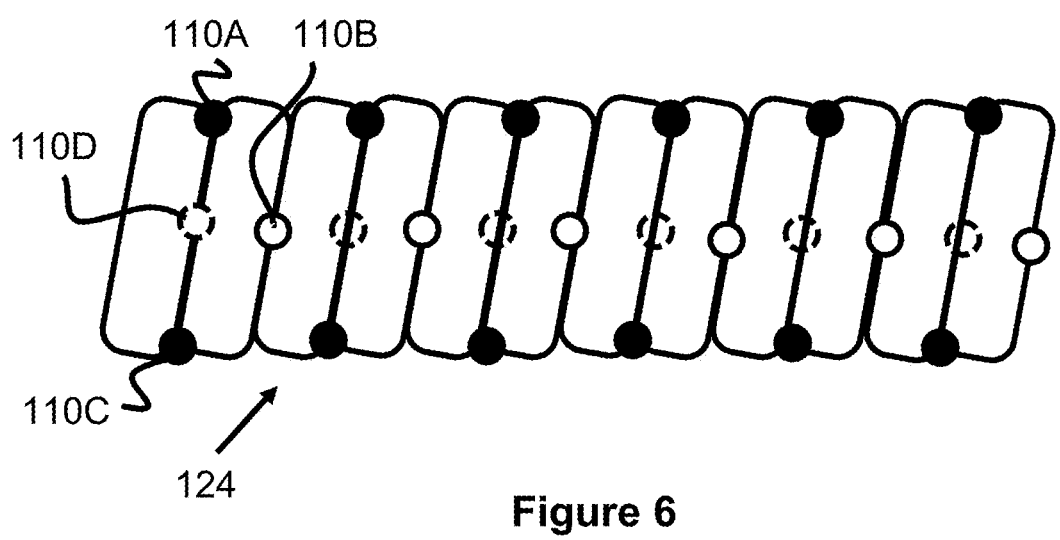

FIG. 6 illustrates another embodiment of a torque transmission element 124 with a differently distributed weld point 110 pattern than that of element 106. Specifically, the first and second loops have a 0-degree weld point 110A, a 180-degree weld point 110C, and a 270-degree weld point 110D. The second and third loops have a 90-degree weld point 110B. Such a pattern may allow the torque transmission element 124 to have relative stiffness along one axis and greater flexibility along another axis.

Figure 7:
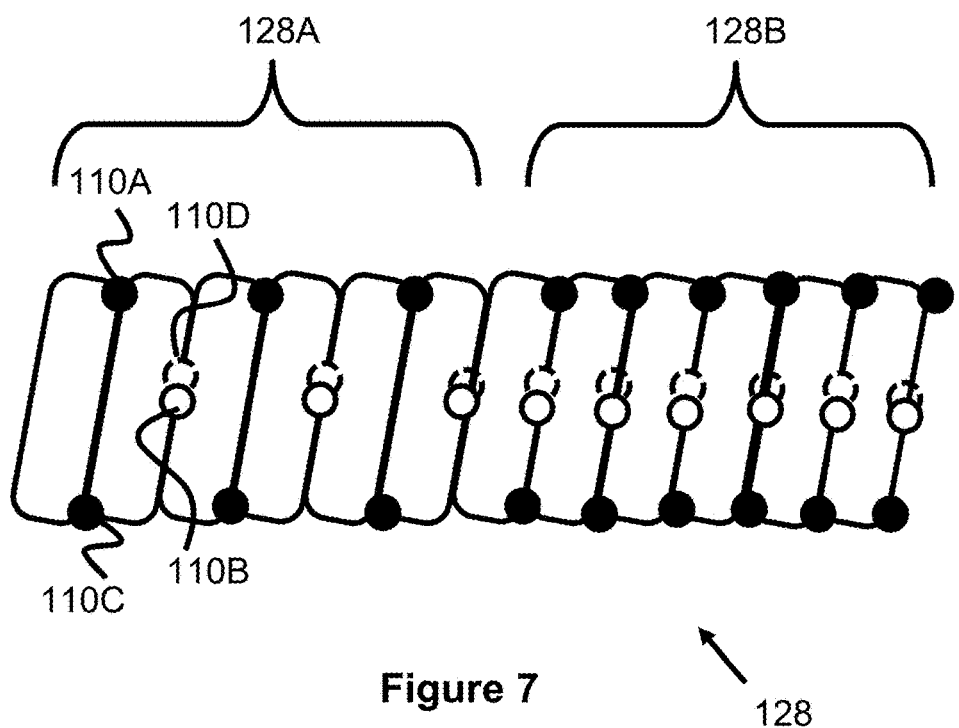
Figure 9:
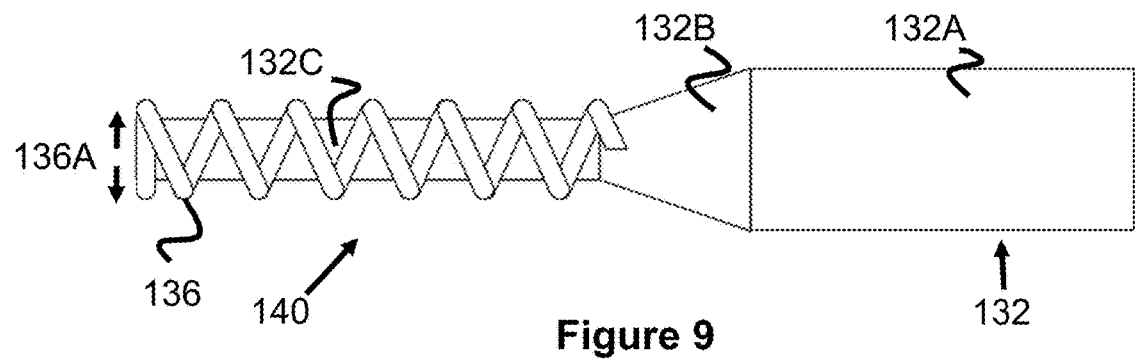

FIG. 7 illustrates another embodiment of a torque transmission element 128 having a first, distal region 128A with a weld point 100 pattern similar to element 106 and a second, proximal region 128B having a weld point 100 pattern similar to element 120. In this respect, the flexibility of the torque transmission element 128 can change along its length, becoming more flexible in the distal direction. While only two regions are illustrated in FIG. 9, a plurality of different regions of different weld point 100 patterns are possible (e.g., 3-10 regions). Alternately, instead of abrupt, distinct regions, a pattern can be created in which the distance between weld points 110 progressively increases or decreases in the distal direction. Hence, the flexibility may progressively and gradually increase in the distal direction of the torque transmission element instead in discrete regions.

Figure 8:
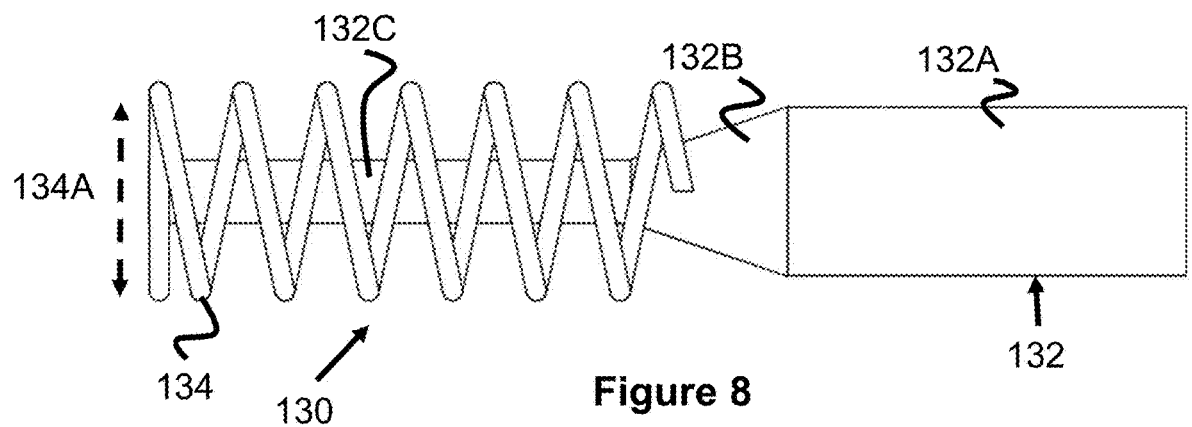
FIGS. 8-15 illustrate side views of different guidewires with shaft elements and torque transmission elements according to the present invention.

FIGS. 8-15 illustrate various embodiments of guidewires that each have a different shaft element and/or size and position of the torque transmission element (note that any of the torque transmission elements described in this specification can be used with these shaft elements). Turning first to FIG. 8, a guidewire 130 comprises a shaft element 132 and a torque transmission element 134. The shaft element 132 includes a proximal, larger diameter portion 132A, a distal reduced diameter portion 132C, and a tapered portion 132B located between the previous two portions 132A, 132C. The torque transmission element 134 has a proximal end that terminates and is connected to the tapered portion 132B and a distal end that terminates near the distal end of the reduced diameter portion 132C of the shaft element 132. The torque transmission element 134 preferably has a diameter that is about the same as the diameter of the larger diameter portion 132A of the shaft element 132. The torque transmission element 132 can be connected to the shaft element 132 at its proximal end, its distal end, and/or at locations along its length. Along most of its length, the torque transmission element 132 is spaced apart from the reduced diameter portion 132C by way of an open gap or by the inclusion of other material layers.

FIG. 9 illustrates a guidewire 140 that is generally similar to guidewire 130, except that the torque transmission element 136 has a relatively smaller diameter 136A that is smaller than portion 132A of the shaft element 132. Additionally, the relatively smaller diameter 136A of the torque transmission element 136 may be such that the inside surface of its coils partially or fully contact portion 132C of the shaft 132 (or optionally another layer of material. Both the smaller diameter 136A and the additional contact points of the torque transmission element 136 may increase the stiffness and reduce the flexibility of the distal end of the guidewire 140 relative to the guidewire 130.

Figure 10:
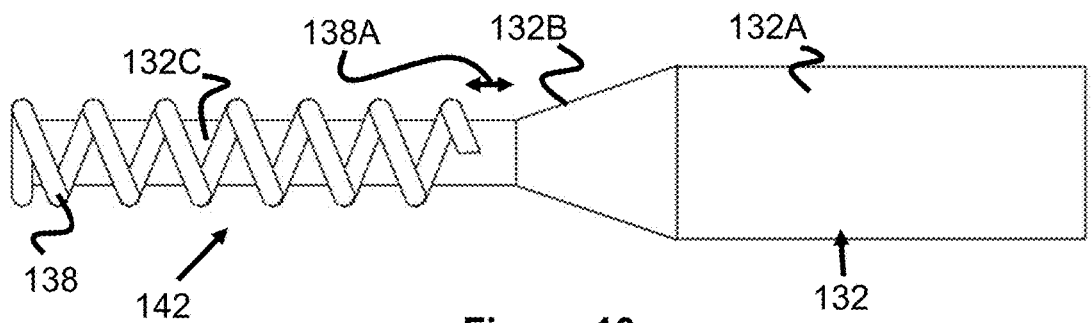

FIG. 10 illustrates a guidewire 142 that is generally similar to guidewire 140, however the torque transmission element 138 has a proximal termination point that is distally spaced apart from the tapered portion 132B of the shaft element 132 (distance 138A). Reducing the length of the torque transmission element 138 along the reduced diameter portion 132C may provide additional flexibility or possibly a region of additional flexibility (i.e., distance 138A).

Figure 11:
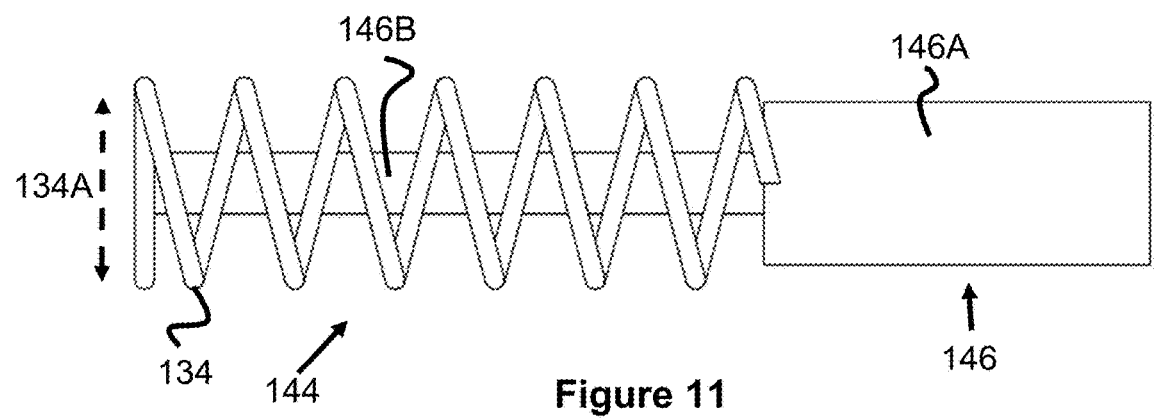

FIG. 11 illustrates a guidewire 144 that is generally similar to guidewire 130, except that the shaft element 146 has only a proximal, larger diameter portion 146A and a distal, smaller diameter portion 146B, but no tapered portion. This transition of the shaft element 146 may provide a more abrupt transition to the distal flexible portion of the guidewire 144.

Figure 12:
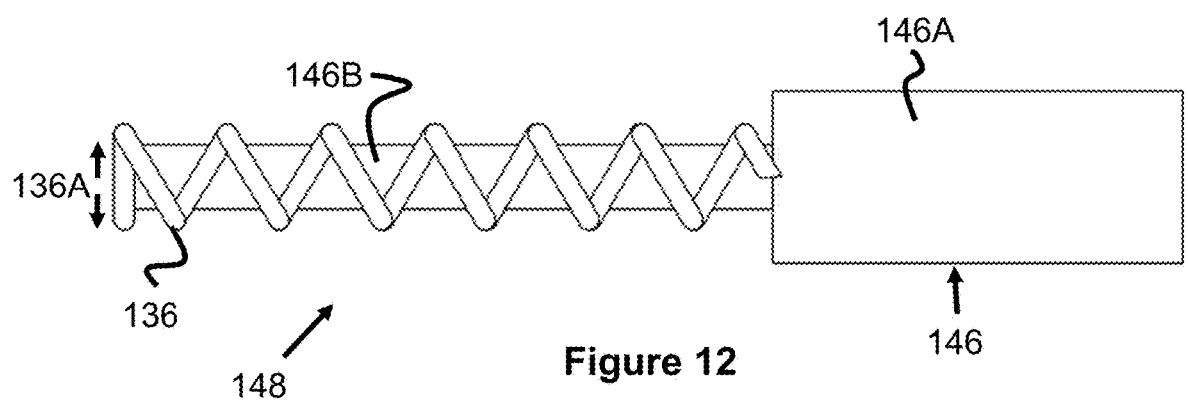

FIG. 12 illustrates a guidewire 148 that has a similar shaft element 146 as guidewire 144 and a similar torque transmission element 136 as guidewire 140.

Figure 13:
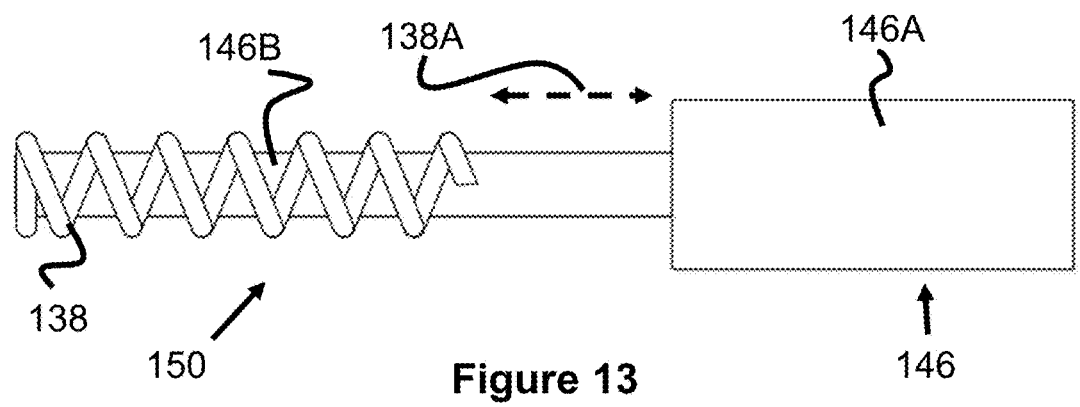

FIG. 13 illustrates a guidewire 150 that has a similar shaft element 146 as guidewire 144 and a similar torque transmission element 138 as guidewire 142. However, since the shaft element 146 lacks the tapered region 132B of guidewire 142, the result is a longer, distal portion of the smaller diameter portion 146B that is not coaxial or surrounded with the torque transmission element 138 (length 138A) and therefore may result in greater flexibility in this region.

Figure 14:
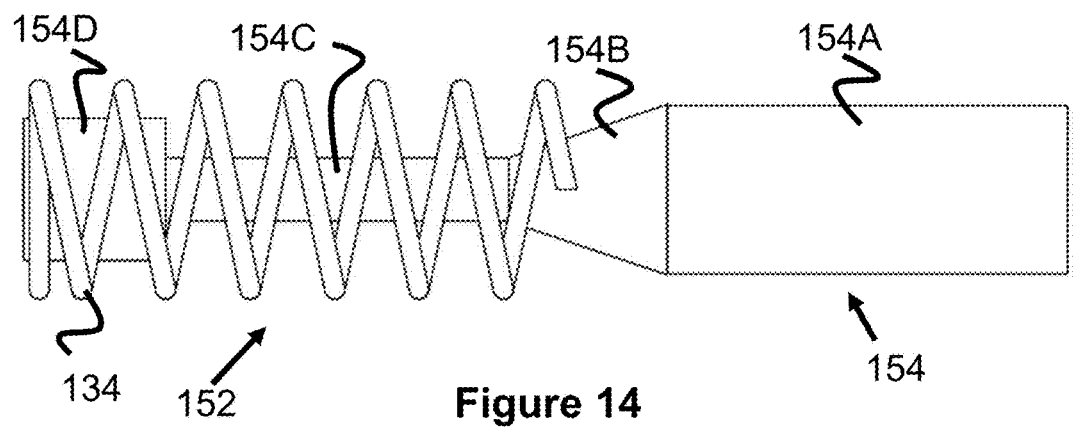

FIG. 14 illustrates a guidewire 152 that has a similar torque transmission element 134 as guidewire 130. However, the shaft element 154 includes a larger diameter distal portion 154D, in addition to the smaller diameter portion 154C, tapered region 154B, and larger diameter portion 154A. The distal end of the torque transmission element 134 may be fixed to the portion 154D or simply surround it by connecting only at the tapered portion 1546. Generally, the additional diameter thickness of the portion 154D may provide decreased flexibility, especially at the immediate distal end of the guidewire 152, as well as a larger and potentially attachment point for the torque transmission element 134.

Figure 15:
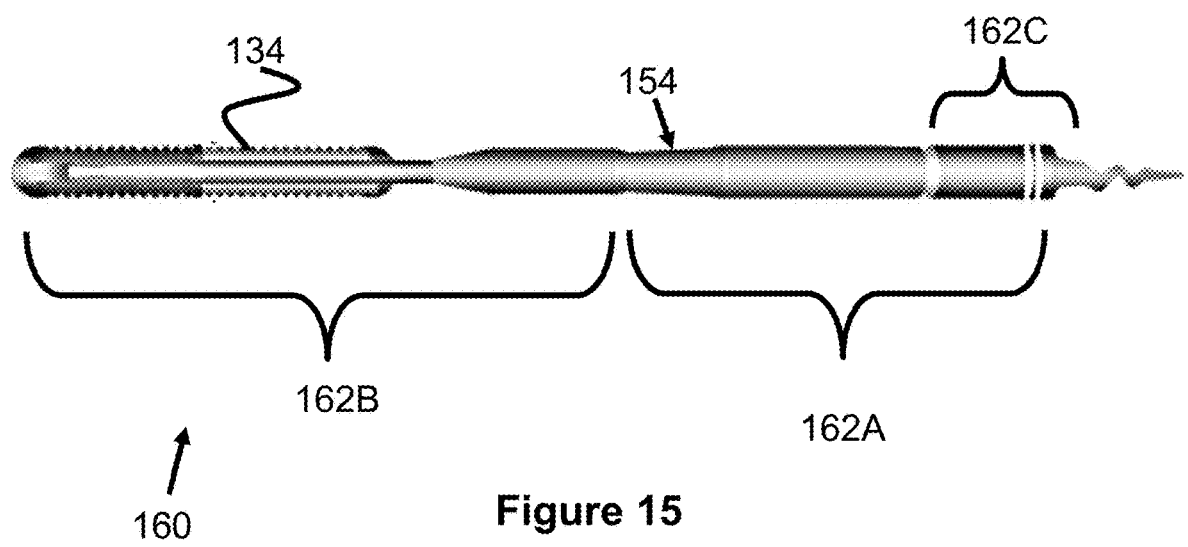

FIG. 15 illustrates a guidewire 160 that is generally similar to guidewire 130. However, region 162A of the shaft element 154 is preferably composed out of stainless steel and is about 140 cm in length, region 162B is preferably composed out of Nitinol and is about 60 cm in length, and the proximal end of the shaft element 154 includes a docking region of about 2 cm (for connecting to a proximal handle or to an extension system to extend the overall length of the guidewire). The regions 162A and 162B are preferably directly connected to each other in a direct joint (e.g., by welding or similar attachment mechanisms). Additionally, the region 162B (including the torque transmission element 134) are preferably coated in a hydrophilic coating or PTFE layer to better prevent blood from coating or sticking to the guidewire 160 and to reduce friction of the device within the patient.

In the embodiments of this specification, element 110 is referred to as a weld. This weld can be achieved via laser welding, spot welding, or other traditional welding techniques. The weld may be an area of high temperature created to melt portions of the wire 108 or may include melting an additional material between two regions of the wire 108. Alternately, the welds may be a short longitudinal wire having one end welded to one coil loop and a second end welded to a second coil loop.

Preferably, the wire 108 of the various torque transmission elements are comprised of stainless steel, platinum, tantalum, gold, nitinol, cobalt-chromium, or combinations of these materials. Preferably, the wire 108 has a circular diameter, however, the wire 108 may also have an oval or generally flat diameter (e.g., a ribbon).

The embodiments of the torque transmission element have been described as a helically wound wire 108 which can take the shape of a coil having a plurality of loops 107. However, it is also contemplated that the torque transmission element may include multiple, distinct, longitudinally aligned coils of helically wound wire 108 that are either connected at their ends or spaced apart from each other. In another embodiment, the torque transmission element may include multiple layers of coils of helically wound wire 108, such as an inner helically wound wire 108 and an outer helically wound wire 108. In another embodiment, the torque transmission element may be composed of a plurality of braided wires 108. In another embodiment, the torque transmission element may be composed of a combination of helically wound coils, helically wound ribbons, and/or a braided mesh.

Preferably, the shaft elements of the present specification are composed of stainless steel, nitinol, cobalt-chromium, nickel-cobalt, nitinol alloys, nitinol-stainless steel alloy, or other similar materials. The shaft elements can be composed of a single material or regions of different material that are attached together.

Generally, welding or attaching two loops 107 together will increase the stiffness and strength of the torque transmission element in this region, since the windings will be connected and the flexibility will be decreased in the attachment region. One advantage of varying the weld or attachment points on different portions of the torque transmission element is to vary the areas where the stiffness is increased. Having the attachment locations only, for example, toward the top of the windings would localize the high strength zones within that particular section of the guidewire. It is generally desirable to spread out the high strength areas throughout the torque transmission element so that the high strength areas are not concentrated in one particular region of the torque transmission element—that is, it is generally desirable to have alternating portions of high strength/high stiffness (attachment) and high flexibility (no attachment) throughout the torque transmission element. The previously discussed embodiments may accomplish this by spreading the attachment locations among different portions of the coil throughout the torque transmission element.

Other torque transmission element examples could utilize the welds or attachments only on the same circumferential angle of the coils (e.g., the weld points are only at the points 110A, 1106, 110C, or 110D), or a more variable profile (e.g., a group of weld points toward the points 110A, 1106, 110C, or 110D; or, varying the weld points at the points 110A, 1106, 110C, or of the windings throughout the length of the torque transmission element). Other examples could have some region where more coil windings are attached together, and some other regions where fewer of the coil windings are attached together in order to vary the strength and flexibility of the guidewire in various locations along the guidewire.

The weld or attachment pattern and locations can also vary depending on how stiff one wants the guidewire. For a completely flexible guidewire, few or no attachments may be used—however, this may negatively affect the push strength and torque response. For a stiffer guidewire, frequent attachments can be used—but this may negatively affect flexibility. The attachments would connect subsequent windings in a select location. For a radially larger torque transmission element, subsequent windings could be attached together at multiple locations along the same winding to enhance radial strength at those select locations (i.e. attaching along both the top and bottom part of subsequent windings). The attachment pattern may skip a few windings in-between, fewer or more attachments can be used where the coil windings are attached, etc. In other words, selective areas of the torque transmission element have locally enforced stiffness by attaching adjacent windings of the torque transmission element together at select locations.

In one example, the weld pattern of the torque transmission element becomes more spaced at the more proximal portions of the torque transmission element. This can be done by selectively skipping attaching winding sections together (e.g., attaching one or two winds over than what was done in the previous section). Having a portion of the torque transmission element with a denser attachment/weld configuration allows that particular section of the torque transmission element to be relatively stiffer. Having a portion of the torque transmission element with a less frequent weld configuration allows that particular section of the torque transmission element to be relatively more flexible, since the coil would retain its natural, gapped spacing in these areas. In this way, the flexibility of the guidewire can be customized.

In one example, the torque transmission element of the guidewire has a stiffer distal section and a more flexible proximal section, where the weld pattern gets less dense from the distal to the proximal end of the guidewire. In another example, the torque transmission element of the guidewire has a more flexible distal section (e.g., less frequent welding pattern) and a stiffer proximal section (e.g., more frequent welding pattern). In another example, various regions of the torque transmission element have differing stiffness profiles. Thus some sections may utilize a less frequent welding pattern and other sections may utilize a denser welding pattern. In another example, a proximal section of the torque transmission element has a more flexible proximal section, the middle section of the torque transmission element is relatively stiffer, and the distal section of the torque transmission element is relatively more flexible. This stiffness variation is accomplished by varying the attachment (i.e. welding) pattern in different sections of the torque transmission element.

The previously described torque transmission elements and shaft elements are preferably connected to each other. Alternatively, the torque transmission element and shaft element could be linked through one or more connecting structures. The operating principle of the device is that the rotation of the shaft element—imbued by the rotation of the user's hand—will result in rotation of the torque transmission element. A portion of the shaft element, in one example, could taper down in diameter to a reduced-diameter section to accommodate the torque transmission element, and the torque transmission element is placed over the reduced-diameter section of the shaft element. The reduced-diameter section continues through the length of the guidewire and is located under the torque transmission element. The proximal end of the torque transmission element contacts the shaft element, while the reduced-diameter section of the shaft element sits within the inner channel of the torque transmission element but does not generally contact said torque transmission element. In this embodiment, the rotation of the torque transmission element is imparted due to the proximal end of the torque transmission element contacting the shaft element.

Other embodiments could utilize a reduced-diameter shaft element section which is sized up to contact the torque transmission element (or, alternatively, a torque transmission element which is sized down to contact the reduced-diameter shaft section). The proximal end of the torque transmission element could still contact the shaft element (as contemplated in the earlier embodiment), or could not contact the shaft element. Where the torque transmission element contacts the reduced-diameter section of the shaft element, the rotation of the torque transmission element resulting from rotating the shaft element is primarily driven through the reduced-diameter section of the shaft element contacting the torque transmission element.

The torque transmission element is preferably connected to the shaft element by means such as soldering, welding, adhesive glue, or mechanical crimp lock.

The guidewire embodiments may be coated with a polymer (e.g. PTFE) or a hydrophilic coating to minimize friction. Where a polymer such as PTFE is used, the torque transmission element may first be coated with the polymer and then coiled (where the torque transmission element is a coil). A similar approach may be used where a hydrophilic coating is used. Alternatively, the coating may be applied after the coil is created. Since hydrophilic substances soften when exposed to blood, the coating will "wet" upon exposure and not maintain the coil in the same state as when the coating was applied (i.e. will not longitudinally restrict movement of the coil windings). Thus the coil may have a degree of "give" to compress or expand. The entire guidewire or just a portion of the guidewire may utilize the coating.

In one example, the total guidewire length (which includes at least the shaft element and the torque transmission element) is about 175 to about 300 centimeters and the torque transmission element length is about 5 to about 40 centimeters.

Any figures shown and descriptions of such figures are meant to be illustrative and not limited solely to what is actually shown or literally described. Any measurements and/or materials described are meant to be illustrative to help describe the various embodiments and are not meant to be expressly limited to what is literally described.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A guidewire consisting of:
   a proximal shaft portion having a uniform first diameter extending along its entire length;
   a tapered shaft portion diametrically narrowing from the first diameter to a smaller, second diameter along its entire length; the tapered shaft portion being immediately located and connected to a distal end of the proximal shaft portion;
   a distal shaft portion being diametrically sized to be the second diameter extending along its entire length; the distal shaft portion being immediately located and connected to a distal end of the tapered portion;
   a coiled wire having a proximal end connected at the tapered shaft portion and extending around the distal shaft portion and entirely along the length of the distal shaft portion; an outer diameter of the coiled wire being equal to the first diameter and an inner diameter of the coiled wire being greater than the second diameter, so as to create a uniform gap along the entire length of the distal shaft portion; the coiled wire terminating at a distal end of the distal shaft portion;
   wherein at least some adjacent loops of the coiled wire are selectively welded together with one or more weld locations along the distal shaft portion to increase stiffness of the torque transmission element; wherein the one or more weld locations comprise a repetitive pattern of a first loop and an adjacent second loop connected together by a first weld point and a second weld point located diametrically across from the first weld point, and a third weld point and a fourth weld point located diametrically across from the third weld point; the third weld point and the fourth weld point connecting the second loop and a third loop adjacent to the second loop; the third weld point and the fourth weld point being located at 90 degrees relative to either the first weld point or the second weld point.

2. A guidewire consisting of:
   a shaft comprising a proximal shaft portion immediately distally followed and connected to a tapered shaft portion, the tapered portion immediately distally followed and connected to a distal shaft portion;
   wherein the proximal shaft portion has a uniform first diameter extending along its entire length;

wherein the distal shaft portion has a second diameter extending along its entire length, the second diameter being smaller than the first diameter of the proximal shaft portion;

wherein tapered shaft portion tapers between said first diameter and said second diameter;

a helical coil connected over to the distal shaft portion, where the helical coil includes a plurality of loops; the plurality of loops extending around the distal shaft portion and entirely along the length of the distal shaft portion; an outer diameter of the helical coil being equal to the first diameter of the proximal shaft portion; the helical coil creating a uniform gap along the entire length of the distal shaft portion and terminating at a distal end of the distal shaft portion;

wherein at least some adjacent loops of the plurality of loops are selectively attached to each other via weld points that are positioned in a repetitive pattern along at least a portion of the length of the helical coil to decrease the flexibility of the helical coil;

wherein the repetitive pattern of the weld points comprises repeating circumferential positions of the weld points along the helical coil;

wherein the repetitive pattern comprises a first and second weld point connecting a first and second loop of the plurality of loops and being spaced 180 degrees apart from each other; and wherein the repetitive pattern further comprises a third and fourth weld point connecting the second loop and a third loop, the third and fourth weld points being spaced 180 degrees apart from each other and 90 degrees from the first and second weld points.

3. A guidewire consisting of:

an elongated shaft comprising a proximal shaft portion immediately distally followed and connected to a tapered shaft portion, the tapered portion immediately distally followed and connected to a distal shaft portion;

wherein the proximal shaft portion has a uniform first diameter extending along its entire length;

wherein the distal shaft portion has a second diameter extending along its entire length, the second diameter being smaller than the first diameter of the proximal shaft portion;

wherein tapered shaft portion tapers between said first diameter and said second diameter;

a helical coil disposed over the distal shaft portion, where the helical coil comprises a plurality of loops; the plurality of loops extending around the distal shaft portion and entirely along the length of the distal shaft portion; an outer diameter of the helical coil being equal to the first diameter of the proximal shaft portion; the helical coil creating a uniform gap along the entire length of the distal shaft portion and terminating at a distal end of the distal shaft portion;

wherein at least some adjacent loops of the plurality of loops are selectively attached to each other via weld points that are positioned in a longitudinal pattern of circumferential locations along at least a portion of the length of the helical coil to decrease the flexibility of the helical coil;

wherein said longitudinal pattern of circumferential locations comprises a first and second weld point connecting a first and second loop of the plurality of loops and being spaced 180 degrees apart from each other; and wherein the repetitive pattern further comprises a third and fourth weld point connecting the second loop and a third loop, the third and fourth weld points being spaced 180 degrees apart from each other and 90 degrees from the first and second weld points.

* * * * *